United States Patent
Lombardi

(10) Patent No.: US 7,404,404 B2
(45) Date of Patent: Jul. 29, 2008

(54) ANTERIOR SEXTANT DENTAL BITE TRAY APPARATUS

(75) Inventor: Drew R. Lombardi, Demarest, NJ (US)

(73) Assignee: LBB Enterprises, LLC, Demarest, NJ (US)

( * ) Notice: Subject to any disclaimer, the term of this patent is extended or adjusted under 35 U.S.C. 154(b) by 457 days.

(21) Appl. No.: 10/835,172

(22) Filed: Apr. 29, 2004

(65) Prior Publication Data

US 2005/0241650 A1   Nov. 3, 2005

(51) Int. Cl.
*A61C 3/00* (2006.01)
*A61C 5/14* (2006.01)

(52) U.S. Cl. .............................. 128/861; 128/859; 433/6

(58) Field of Classification Search ................ 128/861, 128/848, 859–862; 602/902; 433/6, 37, 433/41–43, 80, 89
See application file for complete search history.

(56) References Cited

U.S. PATENT DOCUMENTS

| | | | | |
|---|---|---|---|---|
| 646,629 A | * | 4/1900 | Sugatt .............................. 433/6 |
| 2,857,909 A | * | 10/1958 | Johnson ........................ 128/861 |
| 3,536,069 A | * | 10/1970 | Gores ........................... 128/861 |
| RE28,667 E | * | 12/1975 | Gores ........................... 128/861 |
| 4,114,614 A | * | 9/1978 | Kesling ........................ 128/861 |
| 4,139,944 A | | 2/1979 | Bergersen |
| 4,173,219 A | * | 11/1979 | Lentine ......................... 128/861 |
| 4,173,505 A | * | 11/1979 | Jacobs ........................... 433/89 |
| 4,305,709 A | * | 12/1981 | Bruhn et al. .................. 128/861 |
| 4,376,628 A | * | 3/1983 | Aardse .......................... 433/80 |
| 4,898,535 A | | 2/1990 | Bergersen |
| 5,028,231 A | * | 7/1991 | Hall .............................. 433/6 |
| 5,067,896 A | * | 11/1991 | Korn ............................. 433/6 |
| 5,876,199 A | | 3/1999 | Bergersen |
| 5,895,218 A | * | 4/1999 | Quinn et al. ................... 433/80 |
| 5,957,686 A | | 9/1999 | Anthony |
| 6,364,659 B1 | | 4/2002 | Lotte |
| 6,604,527 B1 | * | 8/2003 | Palmisano ................... 128/848 |
| 6,626,664 B1 | * | 9/2003 | Bergersen ....................... 433/6 |

* cited by examiner

*Primary Examiner*—Kim M Lewis
(74) *Attorney, Agent, or Firm*—Duane Morris LLP

(57) ABSTRACT

An intraoral, flexible, hinged appliance which is an anterior resistance appliance, covering both anterior sextants of both arches (jaws), having the effect of an anterior bite plane, to facilitate orthodontic treatment. Each of the hinged sections consists of a roughly semicircular trough or tray that fits over the anterior sextant of a patient's teeth. The two troughs are hinged at the rear with a flexible material that when the troughs are flexed together and inserted in the mouth causes a force tending to lock the troughs against the patient's teeth, thereby helping to open a deep bite and protect teeth from the negative affects of bruxism or teeth grinding, and to relieve temporomandibular joint pain and dysfunction.

10 Claims, 2 Drawing Sheets

ANTERIOR SEXTANT DENTAL BITE TRAY APPARATUS

FIELD OF THE INVENTION

The invention relates to dental devices used to correct malocclusions or to prevent the harmful effects of bruxism or tooth grinding or clenching. More particularly, the invention relates to devices that are worn in the mouth on a part-time basis. In addition, the invention relates to dental devices used to relieve symptoms of temporomandibular joint disorders (or TMD) resulting from malocclusion, accident or injury.

BACKGROUND OF THE INVENTION

Deep bite, commonly referred to as an overbite, is one of the most common dental malocclusions. In patients who have deep bite, the lower front teeth (mandibular anteriors) close deep behind the upper front teeth (maxillary anteriors). This condition causes a number of problems. Because the lower front teeth do not close in alignment with the upper front teeth, the lower jaw (mandible) closes too far up, i.e. autorotates up, or comes too close to the upper jaw. This is usually due to extra pressure on the back teeth, which causes them to recede (intrude) into the gum, or to never fully erupt properly, or to be ground down, bruxed or worn. (It may also be due to missing posterior teeth, due to caries or periodontal problems.) The further the back teeth recede (intrude) into the gum the more the lower front teeth undercut the upper front teeth. As the lower front teeth cut higher behind the upper front teeth, they are pushed back, along with the lower jaw, because the backs of the upper front teeth are thicker at their base (at the gum line) than at their incisal edge. The top front teeth are sometimes pushed forward and are spaced apart. As a result, there is less space in this inter-canine region, causing the lower front teeth to crowd in order to fit there. In addition to creating an ineffective bite, the misalignment of the lower front teeth behind the upper front teeth can cause crowding of the lower teeth as they are pushed back by the upper front teeth. Because the misalignment also forces the mandible toward the back of the head, these forces can result in painful conditions of the temporomandibular joint, called TMJ or TMD.

Deep bite can arise for many reasons, the most common being nocturnal, and occasionally waking, clenching and grinding (bruxism) of the teeth, which both wears down and intrudes the back teeth. Accidents and loss of rear teeth due to decay and periodontal problems can also cause deep bite.

Corrective measures for deep bite aim to "open" the bite, by preventing the lower jaw from closing as close to the upper jaw, and stopping the negative effects of the clenching and grinding of the teeth. As the lower jaw is not closed so tightly and the lower front teeth are not forced backward by the backs of the upper front teeth, the condition can be gradually corrected in that the back teeth, which have been relieved of the pressure of closing on each other, are now able to extrude out of the jaw. Once the back teeth have extruded sufficiently that the lower front teeth are no longer closing on the inward sloping back of the upper front teeth, rearward pressure on the lower jaw is relieved.

Deep bite has been treated for many years by installing in the roof of the mouth a bite plate, also termed a retainer. The bite plate is a custom-made device modeled on a casting of the patient's teeth. The bite plate, which is removable, attaches to the upper teeth with wires shaped to fit the outside of the upper front and back teeth. The device also has a plastic component shaped to fit the roof of the patient's mouth. Together, the wires and the plastic component hold the bite plate in the patient's mouth. The plastic portion of the bite plate extends forward from the roof of the mouth to just behind the upper front teeth. As such, the plastic portion blocks the lower front teeth from closing too far up and behind the upper front teeth. Instead of hitting the backs of the upper front teeth, the lower front teeth hit the plastic part of the bite plate (the anterior bite plane). Because the back teeth are now not closing as fully or tightly as without the plate, they are able to gradually extrude. Also, because the lower front teeth are not closing so far up, they are not pressed as tightly behind the upper front teeth, and there is less cause for crowding of the lower front teeth. Lastly, since the pressure of the bite is now vertically on the smaller lower front teeth mostly, it sends the brain the message to stop clenching so much.

Bite plates are not without problems, however. Being custom made, requiring a mold of the patient's teeth and a poured model, they are costly to make and replace, and because they are removable, are occasionally broken and lost, especially by younger patients. Moreover, because the wire retainer is formed on a casting of the teeth in their uncorrected state, the retainer inhibits or complicates any corrective adjustment while it is being worn, which makes corrective adjustment more difficult.

Another, less common, treatment for deep bite involves the bonding of small blocking devices directly to the back of the upper front teeth. These devices, termed lingual bite blocks, buttons, bite ramps, or Bite Turbos™, function similarly as bite plates in that they prevent the lower front teeth from pressing up against the inside of the upper front teeth. Anthony in U.S. Pat. No. 5,957,686 and Lotte in U.S. Pat. No. 6,364,659 describe two such devices. Lingual bite blocks or buttons can cause chipping of the lower teeth, and occasionally come off, which can be highly dangerous if they are aspirated. Additionally, they too can be expensive, require a model, and are custom made to fit the shape of the patients lingual tooth surface.

SUMMARY OF THE INVENTION

The present invention is a pair of flexibly hinged guards for the upper and lower front teeth (anterior sextants), which fit over the teeth in a similar manner as a sports mouth guard. Unlike a sports mouth guard, however, the present invention fits more loosely over the teeth and can be made of thinner material. Since its function is corrective and not to protect from blows, it does not cover the back teeth. Because the device is loose fitting, it is possible to produce a universally-sized device that can be worn by a large segment of the population. Furthermore, when worn with braces, it does not inhibit orthodontic tooth movement and correction, even on the teeth it covers.

The device only covers the front sextant of the upper and lower arches. When worn, the device prevents the lower front teeth from hitting the rear of the upper front teeth when the jaws are closed. The upper and lower front teeth take all the pressure of the bite. Since the lower front teeth are smaller and more sensitive, the brain tends to decrease the signals causing clenching and bruxing. Because the device does not cover the rear teeth and creates a gap between upper and lower rear teeth when worn, these teeth are relieved of pressure and will extrude over time if the device is worn regularly. The device also disengages the upper and lower molars and bicuspids, which allows them to be orthodontically corrected and to realign without interference. This effect is particularly helpful if the device is used in conjunction with braces, headgear, or elastics. In addition, the device prevents the upper front teeth from contacting any braces that might be installed on the lower front teeth, both protecting the upper teeth's incisal edges and the lower teeth's braces from damage and breakage.

The upper and lower halves of the device are attached to each other by flexible bands or tubes that extend from the side wall of each half to the same side on the other half. The flexible bands can be made of the same material as the device itself as long as the bands are able to bend without losing their shape and can provide some force tending to push the two halves apart when they are folded together as installed in the mouth. The flexible hinge effect, which operates in the opposite direction as a bear trap, not only forces the upper and lower halves of the device to stay pressed against the patient's teeth, but the force also gives a small amount of pressure to help keep the lower jaw from closing as tightly against the upper jaw. This flexible opening force makes the device easier to wear and also eases breathing, speaking and sleeping. Because the upper and lower troughs are connected to the open ends of the U shaped bands or tubes, the troughs are free to open completely when the wearer's mouth is open and a steady pressure is exerted forcing the troughs against the upper and lower teeth, thus keeping the device in place. The U shaped flexible spring also allows the lower jaw to freely move forward and rearward and side to side relative to the upper jaw, thus adding in relief of TMJ discomfort. The flexible spring also permits the lower jaw to find its own comfortable, musculature-guided, best and preferred position.

Bite trays that protect substantially all of the teeth are known in the art. Such devices are generally tight fitting and used to protect against sports injuries. Dental trays that are connected with flexible bands are described in Gores, U.S. Pat. No. Re. 28667 "Double Tray Dental Apparatus." The trays in Gores, however, cover all the teeth. Gores' does not disclose a device covering only the anterior sextant of the arch. The device disclosed in Gores would not aid in correcting deep bite because all of the teeth are equally compressed. A wearer of the Gores device would not experience extrusion of the rear teeth no matter how long the device was worn. In fact, over time, it will cause intrusion of the rear teeth, worsening a deep bite. This is because as the jaw closes, back teeth contact the tray first. For a sports mouth guard, to prevent injury, this is desirable. In fact, some sports mouth guards are designed to contact only the back teeth (i.e. TotalGard® mouth guard).

Bergersen in U.S. Pat. No. 6,626,664 describes an orthodontic appliance made of very soft, pliable material in the form of upper and lower tooth-receiving troughs hinged at the rear. An embodiment of the device for use in children does not cover the first and second permanent molars and is intended to allow those teeth to erupt further out of the gum, thus opening the patient's bite. This device, however, is fixedly hinged at the rear bases of the upper and lower troughs. As such, the upper and lower troughs cannot slide forward or backward or side to side relative to each other and thus the device has the disadvantage that the lower jaw (mandible) is not free to move forward in a natural fashion once the front teeth have been disengaged from the overbite condition. A further disadvantage of the appliance is that it prevents the mouth from opening fully (or falls out when the mouth is opened) due to the fact that the hinge actually prevents the upper and lower troughs from opening at the very rear of the wearer's mouth.

BRIEF DESCRIPTION OF THE FIGURES

The accompanying drawings illustrate preferred embodiments of the invention as well as other information pertinent to the disclosure, in which.

DETAILED DESCRIPTION

Figure 1:
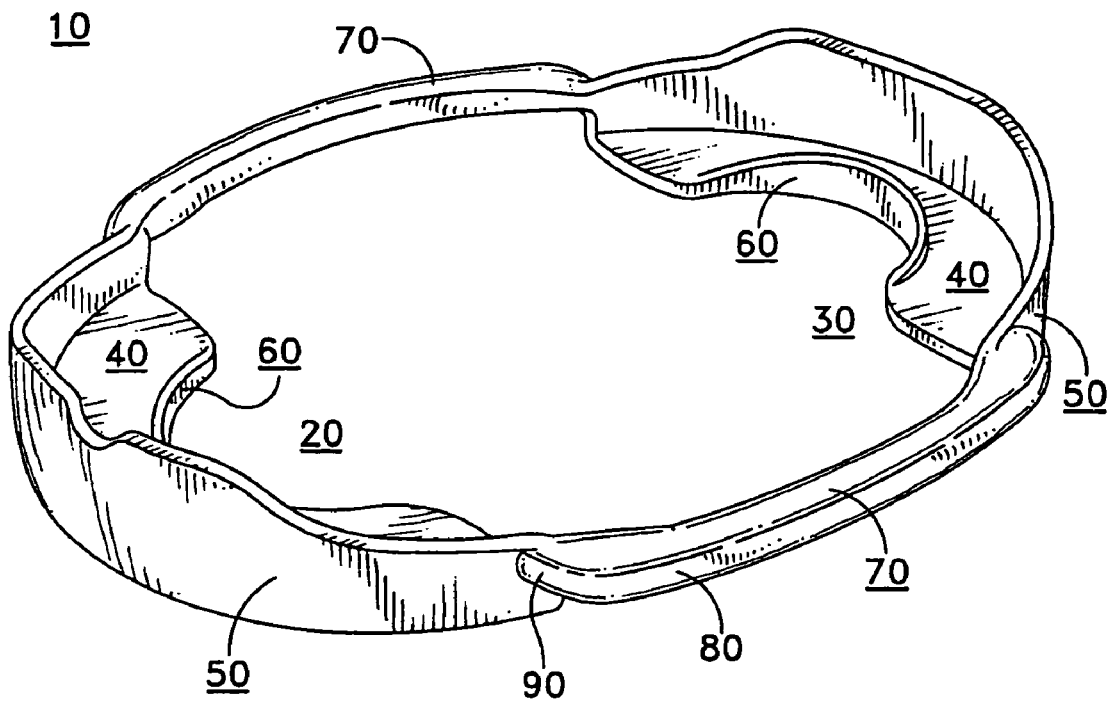
FIG. 1 is an isometric drawing of a dental apparatus constructed according to the present invention and shown in its uninstalled condition.
Figure 2:
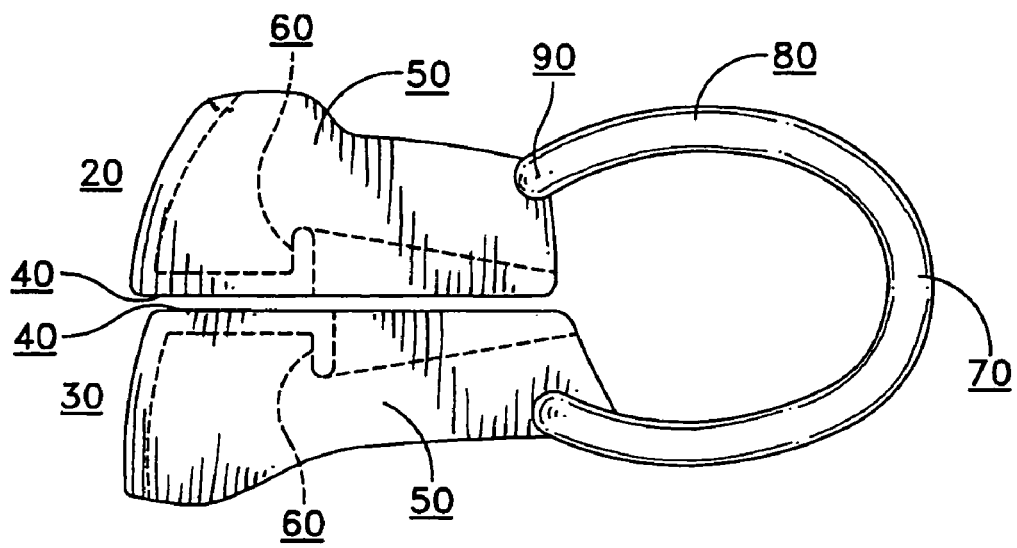
FIG. 2 is a side view of the device configured as it would be in a patient's mouth.
Figure 3:
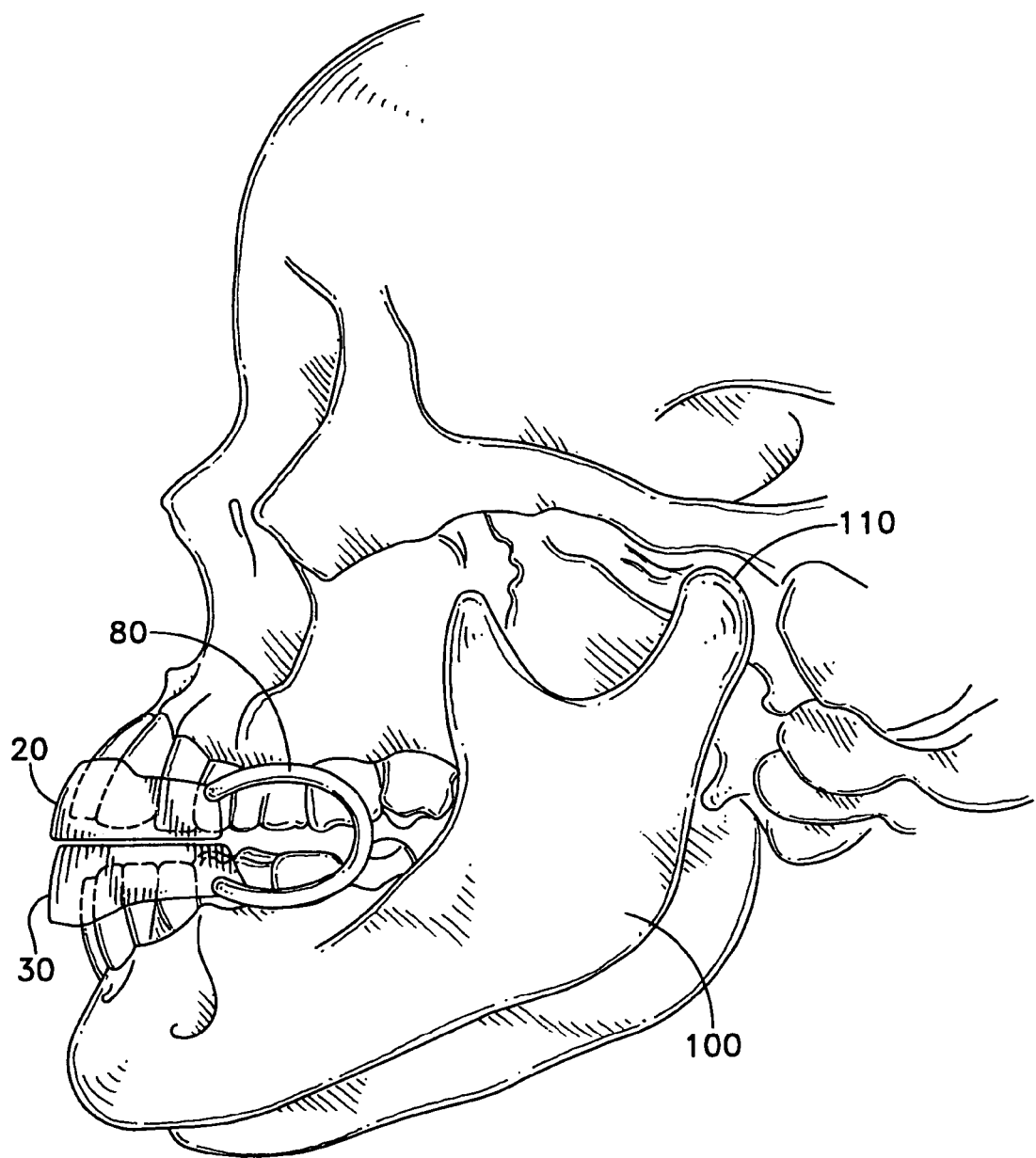
FIG. 3 is a drawing of the device in relation to the teeth and jaw structures when worn.

FIG. 1 illustrates an exemplary version of an intraoral, flexible, hinged appliance according to the invention. The complete device, 10 comprises an upper 20 and lower 30 bite protecting tray connected with two flexible bands 80. Each bite tray is comprised of a base 40 an outer wall 50 and an inner wall 60. FIG. 1 depicts the device in its uninstalled state with the flexible bands 80 fully relaxed. FIG. 2 depicts the device as it would be worn in the mouth, with the flexible bands flexed into a U shape. The resilient bands 80 are connected 90 to the outer walls 50 or extensions of them 55 toward the back of the device.

The resilient bands may have a somewhat thinner section at the middle 70. This thinner section allows the upper 20 and lower 30 bite trays to more easily align themselves with teeth that do not close properly (malocclusion), by enabling the trays to slide forward or rearward or side to side relative to each other, to accommodate the initial malocclusion.

The device is optimally molded as a single piece, with the upper and lower bite trays and the flexible bands produced integrally. Softer plastic materials, such as polyethylene are well-suited to molding techniques that can be employed to manufacture the device as a single unit.

The bite trays are shaped and sized to universally accommodate a majority of patients without the need for maintaining different sizes. This may be accomplished because the arch size of individuals over about eight or nine years of age falls within a relatively narrow range in this section of the mouth. After that age, growth continues in the posterior section of the jaws.

When installed in the mouth, the teeth are cupped by the front 50 and back 60 walls of the device. Some extra play is provided between the front and back walls to allow for crooked and spaced teeth, orthodontic tooth movement, differences in jaw size and tooth size, and patients who are wearing braces. Because of the extra play in the trays, they would not stay attached to the teeth if they were not hinged together by the flexible bands 80. Because the flexible bands have a spring action when folded into a U shape, they force the two halves 20 and 30 apart and toward the respective upper and lower teeth. Outer wall 50 prevents the device from falling too far into the mouth and inner wall 60 prevents the device from pushing out of the mouth. Together the outer and inner walls also give rigidity to each of the bite trays and the outer wall provides an area for attachment of the flexible bands.

When installed in the mouth of a patient with deep bite, the invention prevents the lower front teeth from coming into contact with the back of the upper front teeth. The flat surfaces 40 of each of the halves limit how far the lower jaw can travel (close or autorotate up) and place the lower front teeth at nearly the proper (ideal) vertical distance from the upper front teeth, the only difference being the extra distance created by the thicknesses of the tray bases 40. Because the device only extends rearward to roughly the first bicuspid teeth, the remaining rear teeth (bicuspids and molars) are not in contact with the flat surface 40. Because the device prevents the jaw from closing as far as it would without the device, the rear upper and lower teeth do not come into contact. The resulting space allows the rear teeth to naturally extrude outward from the jaw. Patients who wear the device while sleeping and a few waking hours before bed will eventually have their rear teeth extrude to the point that even without the device, the front teeth no longer contact each other in a deep bite, but close more correctly, now supported by the erupted posterior teeth.

In addition to correcting deep bite by allowing the rear teeth to extrude and by intruding the anterior teeth due to more vertical bite pressure (or at least stopping them from erupting), the device can also relieve rearward pressure on the mandible 100, which causes temporomandibular joint 110 pain and dysfunction and the discomfort that occurs with it. In deep bite, the lower front teeth over close and are pushed toward the posterior, forcing the lower jaw rearward when they close on the inwardly sloping rear of the top front teeth. By separating the lower front teeth from the rear of the upper front teeth, the device instantly relieves this rearward pressure.

The device is also useful in alleviating temporomandibular joint pain that can result from heavy clenching of the muscles of mastication either during sleeping or waking hours. The device stops the mandible from fully closing and also moves the closing pressure from the rear teeth to the front teeth. Because the front teeth, especially the lower front teeth, are more sensitive to pressure than the rear teeth, due to the smaller size of the front teeth, pressure on the front teeth when the device is worn helps stop heavy masseter muscle action by activating the front teeth periodontal ligament proprioceptive pain pathways causing a feedback signal to the brain to reduce pressure on the masseter muscles. This helps to limit the pressure of the clenching.

The flat surfaces 40 serve an additional useful purpose for patients who are wearing braces or other orthodontic devices, such as rubber bands or headgear, intended to realign the molars. Normally, when the lower jaw is closed tightly, the upper and lower molars engage each other, working against any adjustment forces provided by the braces, wires, headgear or other hardware. The present invention, by separating the bicuspids and molars slightly, allows free movement, thus allowing the braces, elastics or headgear to perform their intended alignments with less resistance. The device thereby facilitates orthodontic treatment.

Because the device separates the upper teeth from the lower teeth while allowing free movement between the teeth in each jaw, it is also useful in correcting cross bite. Cross bite is a condition where a tooth is misaligned such that it crosses over its counterpart on the opposite jaw. A typical condition involves an upper tooth that is misaligned inward and which closes behind the corresponding lower tooth. The most difficult aspect of correcting cross bite is "unlocking" the misaligned tooth by opening the bite. For example, in an anterior cross bite, the top (maxillary/upper) front tooth is stuck biting behind the lower (mandibular/bottom) front teeth. The present invention separates the upper and lower teeth, "unlocking" the misaligned upper tooth from the lower teeth that held it in the incorrect position so that braces or wires may be more effective in correcting the tooth's position.

The device also protects both lips from irritation from braces as well as protecting the teeth from the negative effects of tooth grinding or bruxism. When worn during sleep, the device prevents the harmful effects of bruxism by separating the upper and lower teeth. This technique is useful to all patients who exhibit bruxism, not just those with deep bite. It stops the top front teeth's incisal edges from hitting the lower front teeth and their braces, thereby preventing injury and wear to the top front teeth's incisal edges, which are aesthetically most important. It also prevents lower front braces from being broken/fractured off/or damaged. Thereby, preventing orthodontic emergency visits. In patients without front braces, it prevents wear on the incisal edges of the top and bottom front teeth.

The device may also be used to "deprogram" an occlusion prior to taking a bite registration. Dentists and Orthodontists will often make plaster casts of the upper and lower teeth. In order to fully diagnose and assess the patient's condition and prescribe and fit appropriate appliances, dental restorations, crowns, bridges, or dentures, the upper and lower casts must be aligned as they would be in the patient's mouth. This is done by having the patient bite into a soft wax plate or bite registration that records the position of upper and lower teeth relative to each other. For patients who have a misalignment between the upper and lower jaws, such as deep bite, the present invention can be worn for a while in order to "deprogram" the jaw alignment into a more correct or natural position prior to taking the bite registration. This is then a more musculature directed occlusal relationship in harmony with the muscles of mastication, rather than simply a bite registration, which shows how the teeth fit together. Once deprogrammed, the mounted models will show and explain how the jaws would like to fit together absent the malocclusion.

Wearers of the device also experience somewhat of a massage of the periodontal ligament through the alternating compression and relaxation of pressure on the front teeth when the device is bitten down on and then released. This alternating pressure and release cause local ischemia and then hyperemia of the blood supply of the teeth's periodontal ligament, which help to flush out negative chemical byproducts of muscular activity caused by orthodontic force adjustment from braces or other hardware or from grinding and bruxism.

The appliance, being made of a soft material, may be easily adjusted by either the dentist, orthodontist, or patient by simply using a pair of scissors to cut or relieve any area bothering the patient, and then filing it with an emery board to smooth it.

What is claimed is:

1. An intraoral dental apparatus comprising:
    upper and lower trays complementary with at least two upper front teeth and at least two lower front teeth of a wearer, said trays connected together at the rear portion in a non-pivotal manner by flexible elongated members that when placed between said upper and lower front teeth exert a force tending to press the trays against the respective said upper and lower front teeth, said trays further constructed so as to create a gap between at least two pairs of upper and lower rear teeth when the wearer's mouth is fully closed;
    wherein said trays are comprised of an essentially flat base and raised exterior and interior walls;
    further wherein said flexible elongated members are part of a one-piece device wherein said upper and lower trays are integral with the flexible elongated members, said flexible elongated members having a straight shape when the device is at rest, such that the upper and lower trays are in essentially a same plane; and
    further wherein said exterior wall of at least one of said trays extends rearward to a point beyond an end of said flat base and said flexible elongated member attaches to said exterior wall at said point beyond said end of the flat base.

2. The intraoral dental apparatus of claim 1 wherein said one-piece device is a molded device.

3. The intraoral dental apparatus of claim 2 wherein said molded device comprises a resilient plastic.

4. The intraoral dental apparatus of claim 3 wherein said resilient plastic comprises polyethylene.

5. The intraoral dental device of claim 1 wherein the exterior wall of the upper tray has an upper edge that has a gap to accommodate a wearer's maxillary frenum.

6. An intraoral dental apparatus comprising:
upper and lower trays complementary with at least two upper front teeth and at least two lower front teeth of a wearer, said trays connected together at the rear portion in a non-pivotal manner by flexible elongated members that when placed between said upper and lower front teeth exert a force tending to press the trays against the respective said upper and lower front teeth, said trays further constructed so as to create a gap between at least two pairs of upper and lower rear teeth when the wearer's mouth is fully closed;
wherein said trays are comprised of an essentially flat base and raised exterior and interior walls;
further wherein said flexible elongated members are part of a one-piece device wherein said upper and lower trays are integral with the flexible elongated members, said flexible elongated members having a straight shape when the device is at rest, such that the upper and lower trays are in essentially a same plane; and
further wherein a cross-sectional area of said flexible members is smaller for some portion of a mid-length of the flexible members than a cross-section at ends of said flexible members.

7. The intraoral dental apparatus of claim 6 wherein said one-piece device is a molded device.

8. The intraoral dental apparatus of claim 7 wherein said molded device comprises a resilient plastic.

9. The intraoral dental apparatus of claim 8 wherein said resilient plastic comprises polyethylene.

10. The intraoral dental device of claim 6 wherein the exterior wall of the upper tray has an upper edge that has a gap to accommodate a wearer's maxillary frenum.

\* \* \* \* \*